United States Patent [19]

Staniek

[11] Patent Number: 5,986,098
[45] Date of Patent: *Nov. 16, 1999

[54] RELATING TO ORGANIC PROCESSES

[75] Inventor: Peter Staniek, Binzen, Germany

[73] Assignee: Clariant Finance (BVI) Limited, Tortola, Virgin Islands (Br.)

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/901,146

[22] Filed: Jul. 28, 1997

[30] Foreign Application Priority Data

Jul. 30, 1996 [GB] United Kingdom ............ 9615943

[51] Int. Cl.$^6$ .................. G07F 9/06; G07F 9/28
[52] U.S. Cl. ............ 546/25; 524/100; 524/102; 524/103; 546/22
[58] Field of Search ............ 546/22, 25; 524/102, 524/100, 103

[56] References Cited

U.S. PATENT DOCUMENTS 3,904,581 9/1975 Murayama .................. 260/45.8 N
5,616,636 4/1997 Avar ........................ 524/102

FOREIGN PATENT DOCUMENTS 2 202 128 5/1974 France .
2 228 397 10/1995 United Kingdom .

OTHER PUBLICATIONS

Koenig T et al. J. Prakt. Chem. 334 (4), 333–49, 1992.
European Search Report dated Oct. 8, 1997.
T. Konig et al., "Synthesis and N.M.R. Spectroscopy of Organophosphorus Antioxidants and Related Compounds", Journal Fur Praktische Chemie, Chemiker Zeitung, vol. 334, No. 4, 1992, pp. 333–349.

UK Search Report dated Oct. 30, 1996.
Sosnovsky G. and Konteczny M. Synthesis 1978, vol. (8), pp. 583–585.
Konieczny M and Sasnovsky G. Anorg. Chem., Org. Chem., 1978, vol. 33B (9), pp. 1040–1046, "Reaction of Trivalent Organophosphorus Compounds With Selenium".

*Primary Examiner*—Evelyn Huang
*Attorney, Agent, or Firm*—Miles B. Dearth

[57] ABSTRACT

A compound of formula (I) to (III)

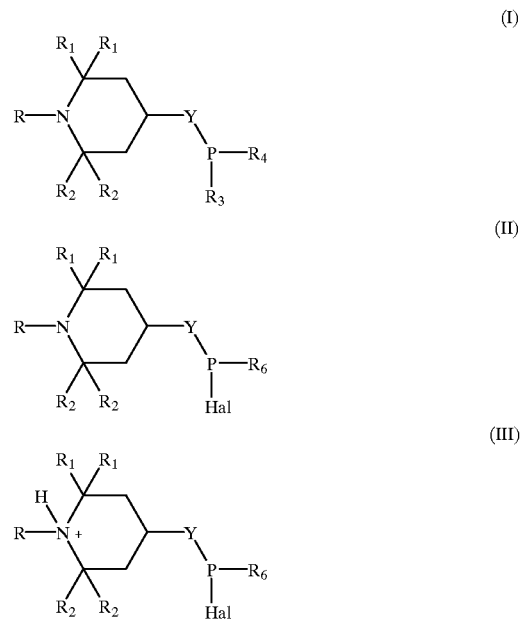

in which the symbols R to $R_6$ are organic radicals. These compounds can be used as intermediates in the production of a phosphite-HALS product.

9 Claims, No Drawings

RELATING TO ORGANIC PROCESSES

Up until now, one of the standard methods for preparing phosphites containing hindered amine light stabilizers (hereinafter defined as "Phosphite-HALS" compounds) is to react a phenol- or alcohol-containing a HALS group with phosphorus trichloride in the presence of a tertiary amine which acts as an acceptor for the liberated HCl.

A voluminous precipitate of the corresponding amine hydrochloride results, which causes stirring problems and so requires the presence of inert solvent or an excess of amine to give a stirrable slurry. After the reaction, this hydrochloride has to be filtered off, which is time consuming and results in loss of product. Filtration and washing with solvent has to be performed under inert conditions, if the highly reactive intermediate is to be isolated for purification.

To overcome this problem, we have discovered new intermediate phosphine compounds for forming these phosphite-HALS.

According to the invention there is provided a compound of formula (I), (II), (III)

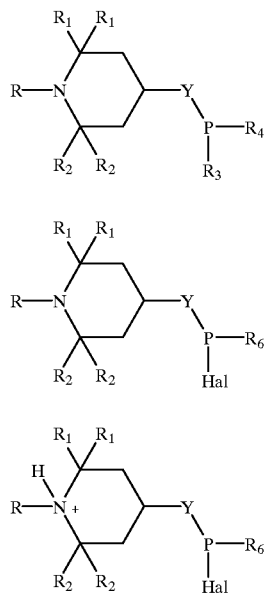

in which

R is hydrogen, —OH, —$C_{1-24}$alkyl, —O—$C_{1-24}$alkyl, —O—CO—$C_{1-24}$alkyl, —O—CO-phenyl, or —CO—$R_7$; where $R_7$ is —CH=$CH_2$, —C($C_{1-4}$alkyl)=$CH_2$, —$C_{1-24}$alkyl, —$C_{1-24}$alkenyl, phenyl, benzyl, —CO-phenyl, —CO—O—$C_{1-24}$alkyl —COOH or $NR_8R_9$; where each $R_8$ and $R_9$ independently is selected from hydrogen, $C_{1-24}$alkyl, $C_{5-12}$cycloalkyl, $C_{6-12}$aryl (preferably phenyl), $C_{6-12}$aryl-$C_{1-12}$ alkyl (preferably phenyl-$C_{1-12}$alkyl) and $C_{1-12}$alkyl-$C_{6-12}$aryl (preferably $C_{1-12}$alkylphenyl); or $R_8$ and $R_9$ form a 4–8 membered ring containing the N-atom and 3–7 carbon atoms. The ring can also contain further heteroatoms such as N, O, S or P;

each $R_1$ is independently $C_{1-5}$alkyl or both groups $R_1$ form a group —$(CH_2)_5$—;

each $R_2$ is independently $C_{1-5}$alkyl or both groups $R_2$ form a group —$(CH_2)_5$—;

$R_3$ is —$NR_8R_9$, where $R_8$ and $R_9$ are defined above;

$R_4$ is a group selected from $R_3$ or $R_5$; where the significance of $R_4$ is independent of that of $R_3$ or $R_5$, where $R_5$ is a group of formula ($\alpha$)

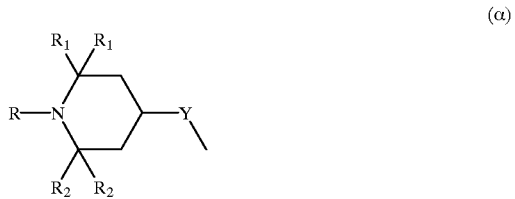

$R_6$ is $R_4$ or Hal;

Hal is Cl or Br, (preferably Cl); and

Y is —O—, —NH— or —N—($C_{1-24}$alkyl)-.

Preferably each $R_1$ and $R_2$ is methyl.

Preferably R is R' where R' is hydrogen, —O—CO-phenyl, —$C_{1-18}$alkyl, —O—$C_{1-18}$alkyl, oxygen or —CO—$R_7$' where $R_7$' is —CH=$CH_2$, $C_{1-8}$alkyl, —CO—$C_{1-8}$alkyl or —CO—O—$C_{1-4}$alkyl.

Preferably $R_3$ is $R_3$' where $R_3$' is selected from di($C_{1-24}$alkyl)amino, di($C_{5-12}$cycloalkyl)amino, di($C_{6-24}$aryl)amino, di($C_{7-24}$alkylaryl)amino or di($C_{7-24}$arylalkyl)amino or —NH($C_{2-24}$alkyl), preferred cyclic derivatives are morpholino and piperidinyl residues.

More preferably $R_3$ is $R_3$" where $R_3$" is —N($C_{2-4}$alkyl)$_2$ or —HN($C_{2-4}$alkyl).

Preferably $R_9$ is $R_9$' where $R_9$' is hydrogen or $C_{1-24}$ alkyl.

Preferably in $R_8$ and $R_9$, aryl is phenyl.

According to a further aspect of the invention, it is possible to prepare compounds of formula (I)

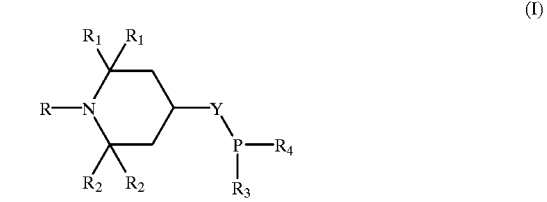

by reacting 1 mole of a compound of formula (II) or (III)

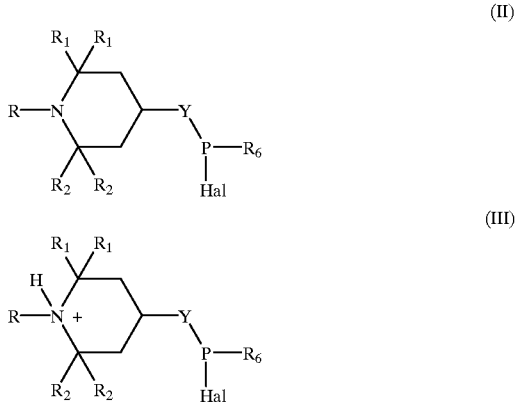

with 1 mole of a compound of formula (IV)

$R_3$—H (IV)

where the symbols are as defined above.

Alternatively and preferably, a compound of formula (I), in which $R_4$ has the same significance as $R_3$, can be prepared by reacting 1 mole of a compound of formula (V)

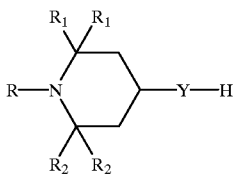
(V)

with one mole of a compound of formula (VI)

$P(R_3)_3$ (VI)

The amino group in $P(R_3)_3$ is preferably derived from a secondary linear, branched or cyclic amine with a boiling point in the range of 30° C. to 150° C.

Compounds of formula (II) can be prepared by reacting, in the presence of tertiary amine, one mole of a compound of formula (V)

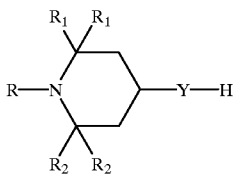
(V)

with 1 mole of a compound of formula (VIII)

$P(Hal)_3$ (VIII)

optionally followed by reacting with 1 mole of a compound of formula (IX)

$R_4$—H (IX)

in which the symbols are as defined above.

Compounds of formula (III) can be prepared by the same process as described above for forming a compound of formula (II) but in the absence of tertiary amine.

Compounds of formula (V) and (VIII) are known or can be made from known compounds by known methods.

Compounds of formula (VI) can be prepared by reacting 6 moles of a compound of formula (VII)

$R_3$—H (VII)

with one mole of a compound of formula (VIII)

$P(Hal)_3$ (VIII)

where Hal is halogen.

3 moles of $R_3$—H are used up binding the liberated HCl. A preferred compound of formula (VIII) is $PCl_3$.

The reaction of a compound of formula (II) or (III) with a compound of formula (IV) to form a compound of formula (I) is carried out at temperatures, −20 to +100° C., more preferably 0–60° C. Optionally a conventional organic solvent may be used.

Compounds of formula (I) can be used to prepare compounds of formula (X) or (XI).

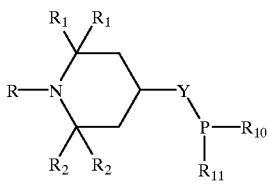
(X)

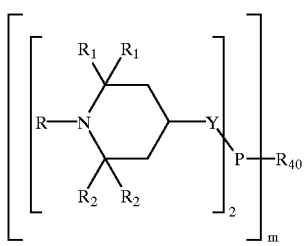
(XI)

in which $R_{10}$ is $C_{1-30}$alkoxy, $C_{2-30}$alkenyloxy, $C_{5-12}$cycloalkoxy, and phenoxy unsubstituted or substituted by 1 to 3 groups selected from $C_{1-24}$alkyl, $C_{1-24}$alkoxy and hydroxy; and $R_{11}$ is a significance of $R_{10}$ or $R_5$, where the significance of $R_{11}$ is independent of $R_{10}$ or $R_5$, where $R_5$ is a group of formula (α) defined above; or $R_{10}$ and $R_{12}$ form a phosphorus containing ring of formula (b)

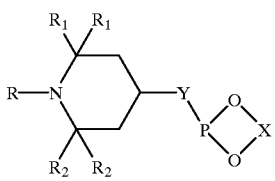
(b)

where X is a group of formula (c)

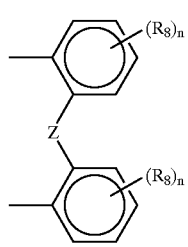
(c)

where $R_8$ is as defined above, n is 0 to 3, Z is —$CH_2$—, —$CH(C_{1-4}alkyl)$-, —$C(C_{1-8}alkyl)_2$-, —O—, —S— or a direct bond.

m is 2 to 4; and when m is 2, $R_{40}$ is —$(OCH_2)_2$—$C(C_{1-12}alkyl)_2$ when m is 3, $R_{40}$ is —$(OCH_2)_3$—$C(C_{1-12}alkyl)$ or —$(OC_{1-12}alkyl)_3$-N or when m is 4, $R_{40}$ is —$(OCH_2)_4$—C.

Compounds of formula (X) are prepared by reacting one mole of a compound of formula (I) with
1 to 2 moles of a compound of formula (XII)

   (XII)

or 1 mole of a compound of formula (XIII)

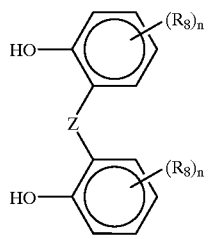   (XIII)

where the symbols are as defined above.
Compounds of formula (XI)

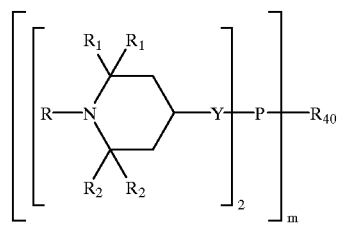   (XI)

can be prepared by reacting m moles of a compound of formula (I)

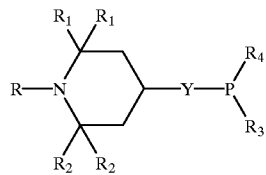   (I)

in which
$R_4$ is $R_5$; and where $R_5$ is a group of formula ($\alpha$)

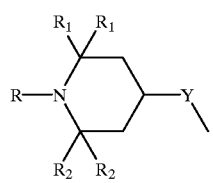   ($\alpha$)

$R_3$ is $-N(C_{1-6}alkyl)_2$ with 1 mole of a compound of formula (XX)

   (XX)

The reaction of a compound of formula (I) with a compound of formula (XII) or (XIII) is preferably carried out at elevated temperatures, preferably from 80–200° C., more preferably at 100–160° C. A solvent may or may not be required dependent on the state of the reactants.

Compound of formula (XII) and (XIII) are known or may be prepared by known methods from known compounds. Compounds of formula (X) and (XI) can also be made from a known compound.

The use of the new compounds of formula (I), (II) or (III) (preferably those of formula (I)) as intermediates offers an attractive possibility for carrying out the reaction with alcohols or phenols to form compounds of formula (X) or (XI) in homogenous solution or even without using solvents. Furthermore, the amount of $R_3$—H (which can be distilled off) gives an useful measure of the reaction. No problematic filtration needs to be performed if compounds of formula (I) are used. The workup and purification can be performed conventionally. The absence of acidic impurities, such as amine hydrochlorides, can improve the hydrolytic and/or thermal stability of the final products, because it is known that such impurities can cause catalytic deterioration of the final compounds under the conditions mentioned.

The phosphite-HALS products (i.e. compounds of formula (X) and (XI)), are well known as processing stabilizers for polymeric materials and as light stabilizers for said polymeric materials.

Polymeric materials that can be stabilized by phosphite-HALS (e.g. compounds of formula (X) or (XI)) include homopolymers, copolymers and polymer blends described in British Patent Application No. 2,276,387 A published Sep. 28, 1994 equivalent to U.S. Pat. No. 5,488,079, or U.S. Ser. No. 08/248282 May 23, 1994, abandoned.

Preferred polymeric materials that can be stabilized are polyolefins, such as polypropylene, polyethylene (e.g. high density polyethylene, low density polyethylene, linear low density polyethylene or medium density polyethylene), polybutylene, poly-4-methylpentene and copolymers thereof as well as polycarbonate, polystyrene and polyurethane.

Also preferred polymeric materials that can be stabilized by compound of formula (X) and (XI) are polyurethanes prepared from isocyanate resins and polyols many of which are commercially available such as those described in GB 2,276,387 A, equivalent to U.S. Pat. No. 5,488,079.

Such polymeric materials are as described in Saechtling: Kunststoff Taschenbuch 23. Ausgabe—published by Carl Hanser Verlag 1986 (esp. p. 339–410). The contents of this book are incorporated herein by reference.

Phosphite-HALS compounds (e.g. compounds of formula (X) or (XI)) may be incorporated by known methods into the polymeric material to be stabilized as described in British Patent Publication No. 2,276,387, equivalent to U.S. Pat. No. 5,488,079.

Phosphite-HALS compounds (e.g. compounds of formula (X) or (XI)) are especially suitable for use in polyolefins and especially $\alpha$-polyolefins prepared using processing catalysts known as Generation II to Generation V catalysts and which have not been subjected to a catalyst removal step, as described in British Patent Publication No. 2,276,387, equivalent to U.S. Pat. No. 5,488,079.

Further, in this specification, where a range is given, the figures defining the range are included therein. Further, any group capable of being linear or branched is linear or branched unless indicated to the contrary.

For the avoidance of doubt, in this specification t-butyl means tertiary butyl, $(-C(CH_3)_3)$.

The contents of British Patent publication No. GB 2,276,387 equivalent to U.S. Pat. No. 5,488,079, and U.S. Ser. No. 08/248282 filed on May 23, 1994, abandoned, are incorporated herein by reference.

The invention will now be illustrated by the following Examples.

EXAMPLE 1

Synthesis of di(1,2,2,2,6-penta-methyl-piperidin-4-oxy)-(diethylamino)phosphine Under inert conditions, 2 moles of 1,2,2,6,6-penta-methyl-piperidin-4-ol are mixed with 1 mole of tris(diethylamino)phosphine and heated to 140° C. over a 6 hour period. During this time, 88% of theory of diethylamine are distilled off. The residue is fractionated in vacuum and the product distills at 156° C./0.05 Torr and yields 55% of a colorless oil which is of di(1,2,2,6,6-penta-methyl-piperidin-4-oxy)-(diethylamino)-phosphine: The chemical shift of substance in the phosphorus NMR spectra, $\delta(^{31}P)$, is as follows: $\delta(^{31}P)=144.3$ ppm.

EXAMPLE 2

Synthesis of di(2,2,6,6-tetra-methyl-piperidin-4-oxy)-(diethylamino)phosphine Under inert conditions 2 moles of 2,2,6,6-tetra-methyl-piperidin-4-ol are mixed with 1 mole of tris(diethylamino)phosphine and heated to 140° C. over a 6 hour period. During this time, 95% of theory of diethylamine is distilled off. The residue is fractionated in vacuum and the product distills at 140° C./0.15 Torr and yields 48% of a colorless oil, which is di(2,2,6,6-tetra-methyl-piperidin-4-oxy)-(diethylamino)phosphine. The chemical shift of substance in the phosphorus NMR spectra is as follows: $\delta(^{31}P)=144.3$ ppm.

EXAMPLE 3

Synthesis of (2,2,6,6-tetra-methyl-piperidin-4-oxy)-bis(diethylamino)phosphine Under inert conditions 1 mole of 2,2,6,6-tetra-methyl-piperidin-4-ol is mixed with 1 mole of tris(diethylamino)phosphine and heated to 130° C. over a 4 hour period. During this time 97% of theory of diethylamine is distilled off. The residue is fractionated in vacuum and the product distills at 89–92° C./0.07 Torr and yields 65% of a colorless oil, which is (2,2,6,6-tetra-methyl-piperidin-4-oxy)-bis(diethylamino)phosphine. The chemical shift of substance in the phosphorus NMR spectra is as follows: $\delta(^{31}P)=131.6$ ppm.

EXAMPLE 4

Synthesis of (1,2,2,6,6-penta-methyl-piperidin-4-oxy)-bis(diethylamino)phosphine Under inert conditions 1 mole of 1,2,2,6,6-penta-methyl-piperidin-4-ol is mixed with 1 mole of tris(diethylamino)phosphine and heated to 130° C. over a 4 hour period. During this time 92% of the calculated amount of diethylamine is distilled off. The residue is fractionated in vacuum and the product distills at 115° C./0.15 Torr and yields 70% of a colorless oil, which is (1,2,2,6,6-penta-methyl-piperidin-4-oxy)-bis(diethylamino)phosphine. The chemical shift of substance in the phosphorus NMR spectra is as follows: $\delta(^{31}P)=131.5$ ppm.

EXAMPLE 5

Synthesis of di(2,2,6.6-tetra-methyl-piperidin-4-yl)-octadec-1-yl-phosphite

Under inert conditions 0.1 mole of di(2,2,6,6-tetra-methyl-piperidin-4-oxy)-(diethylamino)-phosphine is mixed with 0.1 mole of octadecan-1-ol and heated to 160° C. over a 6 hour period. During this time 76% of theory of diethylamine is distilled off. The oily residue is crystallized out by stirring at room temperature with acetonitrile. The yield of di(2,2,6,6-tetra-methyl-piperidin-4-yl)-octadec-1-yl-phosphite is 66%. The chemical shift of substance in the phosphorus NMR spectra is as follows: $\delta(^{31}P)=138.7$ ppm.

I claim:

1. A compound of formula (I), (II) or (III)

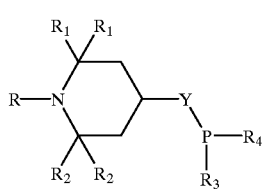

(I)

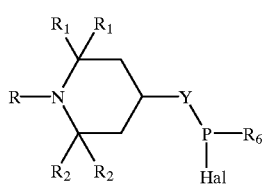

(II)

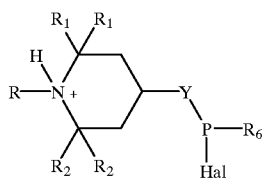

(III)

in which
R is hydrogen, —OH, —$C_{1-24}$alkyl, —O—$C_{1-24}$alkyl, —O—CO—$C_{1-24}$alkyl, —O—CO-phenyl, or —CO—$R_7$; where
$R_7$ is —CH=$CH_2$, —C($C_{1-4}$alkyl)=$CH_2$, —$C_{1-24}$alkyl, —$C_{1-24}$alkenyl, phenyl, benzyl, —CO-phenyl, —CO—O—$C_{1-24}$alkyl; —COOH; or —$NR_8R_9$, where each of $R_8$ and $R_9$ independently is selected from hydrogen, $C_{1-24}$alkyl, $C_{6-12}$cycloalkyl, $C_{6-12}$aryl, $C_{6-12}$aryl-$C_{1-12}$ alkyl or $C_{1-12}$ alkyl-$C_{6-12}$ aryl; or
$R_8$ and $R_9$ form a 4–8 membered ring containing at least one N-atom and from 3–7 carbon atoms said ring optionally containing ring atoms O, S or P;
each $R_1$ is independently $C_{1-6}$ alkyl or both groups $R_1$ form a group —$(CH_2)_5$—;
each $R_2$ is independently $C_{1-5}$ alkyl or both groups $R_2$ form a group —$(CH_2)_5$—;
$R_3$ is —$NR_8R_3$ where $R_8$ and $R_9$ are defined above;
$R_4$ is a group selected from $R_3$ or $R_5$ $_{where\ R5}$ is a group of formula (α)

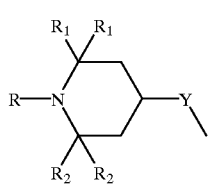

(α)

$R_6$ is $R_4$; and
Y is —O—, —NH— or —N—($C_{1-24}$alkyl)-.

2. A compound according to claim 1 in which $R_3$ is $R_3'$ where $R_3'$ is selected from linear or branched di($C_{1-24}$alkyl)amino, di($C_{5-12}$cycloalkyl)amino, di($C_{6-24}$aryl)amino, di($C_{7-24}$)alkylaryl)amino, di($C_{7-24}$arylalkyl)amino or —NH$C_{2-24}$alkyl, morpholino or piperidino.

3. A compound according to claim 1 in which each $R_1$ and each $R_2$ is methyl.

4. A compound according to claim 1 selected from di(1,2,2,6,6-penta-methyl-piperidin-4-oxy)-diethylamino)phosphine, di(2,2,6,6-tetra-methyl-piperidin-4-oxy)-(diethylamino)phosphine, (2,2,6,6-tetra-methyl-piperidin-4-oxy)-bis(diethylamino)phosphine, and (1,2,2,6,6-penta-methyl-piperidin-4-oxy)-bis(diethylamino)phosphine.

5. A process for using compounds of formula (II) or (III) according to claim 1 for the manufacture of the compounds of formula (X) or (XI)

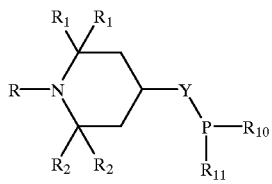
(X)

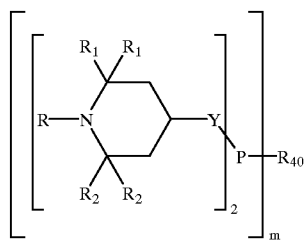
(XI)

in which $R_1$ and $R_2$ are defined in claim 1

$R_{10}$ is $C_{1-30}$alkoxy, $C_{2-30}$alkenyloxy, $C_{5-12}$cycloalkoxy, and phenoxy unsubstituted or substituted by 1 to 3 groups selected from $C_{1-24}$alkyl, $C_{1-24}$ alkoxy and hydroxy; and $R_{11}$ is $R_{10}$ or a group of formula (α)

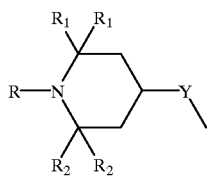
(α)

where

Y is defined as in claim 1; or $R_{10}$ and $R_{11}$ form a phosphorus containing ring of formula (b)

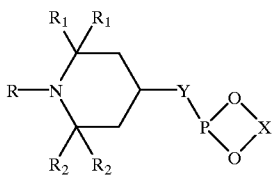
(b)

where X is a group of formula (c)

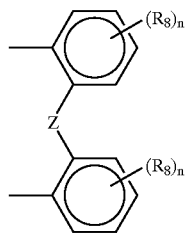
(c)

where $R_6$ is as defined in claim 1, n is 0 to 3,

Z is —$CH_2$—, —$CH(C_{1-4}$alkyl), —$C(C_{1-8}$alkyl)$_2$-, —O—, —S— or a direct bond, m is 2 to 4; and when m is 2, $R_{40}$ is —$(OCH_2)_2$—$C(C_{1-12}$alkyl)$_2$ when m is 3, $R_{40}$ is —$(OCH_2)_3$—$C(C_{1-12}$alkyl) or —$(OC_{1-12}$alkyl)$_3$-N or when m is 4, $R_{40}$ is —$(OCH_2)_4$—C; said process comprising reacting said compounds (II or III) of claim 1 with $R_3$H, wherein $R_3$ is $NR_8R_9$, and wherein $R_8$ and $R_9$ are defined as in claim 1 and further reacting with H—$R_{10}$ to form said (X) or with $H_m$—$R_{40}$ to from said (XI).

6. The process of claim 5 wherein $R_3$ is selected from linear or branched di($C_{1-24}$alkyl)amino, di($C_{5-12}$cycloalkyl)amino, di($C_{6-24}$aryl)amino, di($C_{7-24}$)alkylaryl)amino, di($C_{7-24}$arylalkyl)amino, —NH$C_{2-24}$alkyl, morpholino and piperidino groups.

7. The process of claim 6 wherein $R_3$ is selected from linear di($C_{1-24}$alkyl)amino, linear di($C_{5-12}$cycloalkyl)amino, linear di($C_{6-24}$aryl)amino, linear di($C_{7-24}$alkylaryl)amino, linear di($C_{7-24}$arylalkyl)amino and linear —NH($C_{2-24}$alkyl).

8. The process of claim 6 wherein $R_3$ is selected from branched di($C_{1-24}$alkyl)amino, branched di($C_{5-12}$cycloalkyl)amino, branched di($C_{6-24}$aryl)amino, branched di($C_{7-24}$alkylaryl)amino, branched di($C_{7-24}$arylalkyl)amino and branched —NH($C_{2-24}$alkyl).

9. The process of claim 5 wherein $R_3$ is selected from —N($C_{2-4}$alkyl)$_2$ and —HN($C_{2-4}$alkyl).

* * * * *